United States Patent [19]
Remon

[11] Patent Number: 6,080,427
[45] Date of Patent: Jun. 27, 2000

[54] CEFADROXIL MONOHYDRATE TABLET FORMULATION

[75] Inventor: Jean Paul Louis Auguste Remon, Ghent, Belgium

[73] Assignee: Bristol-Myers Squibb Company, Princeton, N.J.

[21] Appl. No.: 09/042,888

[22] Filed: Mar. 17, 1998

Related U.S. Application Data

[60] Provisional application No. 60/044,140, Apr. 17, 1997.
[51] Int. Cl.$^7$ ...................................................... A61K 9/20
[52] U.S. Cl. ............................................ 424/465; 424/464
[58] Field of Search ...................... 424/464, 465

[56] References Cited

U.S. PATENT DOCUMENTS

| | | | |
|---|---|---|---|
| 3,584,114 | 6/1971 | Cavalli et al. | 424/38 |
| 3,725,556 | 4/1973 | Hanssen et al. | 424/362 |
| 3,873,694 | 3/1975 | Kanig | 424/157 |
| 4,072,535 | 2/1978 | Short et al. | 106/210 |
| 4,414,204 | 11/1983 | Tarcsay et al. | 424/177 |
| 4,439,453 | 3/1984 | Vogel | 424/324 |
| 4,504,657 | 3/1985 | Bouzard et al. | 544/30 |
| 4,851,228 | 7/1989 | Zentner et al. | 424/456 |
| 4,910,023 | 3/1990 | Botzolakis et al. | 424/470 |
| 4,968,508 | 11/1990 | Oren et al. | 424/468 |
| 5,047,246 | 9/1991 | Gallian et al. | 424/464 |
| 5,213,808 | 5/1993 | Bar-Shalom et al. | 424/473 |
| 5,256,440 | 10/1993 | Appel et al. | 427/3 |
| 5,284,662 | 2/1994 | Koparkar et al. | 424/473 |
| 5,366,738 | 11/1994 | Rork et al. | 424/473 |

FOREIGN PATENT DOCUMENTS

| | | |
|---|---|---|
| 181650B1 | 8/1990 | European Pat. Off. . |
| 96/24337 | 8/1996 | WIPO . |

*Primary Examiner*—James M. Spear
*Attorney, Agent, or Firm*—Samuel J. DuBoff

[57] ABSTRACT

This invention relates to uncoated direct compression tablets containing cefadroxil monohydrate as the active ingredient, which are capable of oral administration to human beings by swallowing, chewing or disintegrating in water resulting in a drinkable dispersion.

2 Claims, No Drawings

CEFADROXIL MONOHYDRATE TABLET FORMULATION

This application claims the benefit of U.S. Provisional Application 60/044,140 filed Apr. 17, 1997.

BACKGROUND OF THE INVENTION

1. Field of the Invention

This invention relates to uncoated direct compression tablets containing cefadroxil monohydrate as the active ingredient, which are capable of oral administration to human beings by swallowing, chewing or disintegrating in water resulting in a drinkable dispersion.

2. Background Art

Solid dosage forms, such as tablets and capsules, have been used for many years for orally administering a medicine to a human being.

A problem occurring is the need to protect certain active substances against loss of substance, of potency and/or physico-chemical characteristics due to contact with the atmosphere, recrystallization and/or sublimation. For this purpose, several devices have been constructed, such as sugar-coated, film-coated and compression-coated tablets, capsules and micro-capsules. The latter are quite expensive to produce and also tend to decreased bioavailability, while the other forms of protection hitherto devised, almost by definition, were to be considered incompatible with the principle of the dispersible tablet, i.e. the ability to rapidly disintegrate in water.

Examples of tablets having a core containing active material with a coated outer surface are U.S. Pat. No. 5,366,738 to Rork, et al; U.S. Pat. No. 5,284,662 to Koparkar, et al; U.S. Pat. No. 5,256,440 to Appel, et al; U.S. Pat. No. 5,213,808 to Bar-Shalom et al; U.S. Pat. No. 5,047,246 to Gallian, et al; and U.S. Pat. No. 4,414,204 to Tarcsay, et al.

Additionally, patents relating to controlled-release tablet formulations are U.S. Pat. No. 4,968,508 to Oren, et al; and U.S. Pat. No. 4,851,228 to Zentner, et al.

U.S. Pat. No. 4,910,023 to Botzolakis, et al discloses a tablet containing a drug active in combination with a flavor masking agent.

Besides the solid dosage forms such as tablets, there is also an increasing demand for liquid, drinkable preparations. This is especially the case with the elderly and with children, and the more so when large doses of the medicament are to be taken frequently and/or for extended periods.

Drinkable preparations can sometimes be delivered to the patient already in their liquid form, in solution, suspension or emulsion. This always has obvious logistic disadvantages, and moreover many medicaments tend then to decompose quite quickly.

A good alternative is to supply the medicament in a special solid formulation, which on putting into water will quickly disintegrate to form a mixture which is homogeneous and agreeable enough to be drinkable. Examples are effervescent tablets and dispersion tablets, the former depending on the reaction of bicarbonate or carbonate with an acid or on other excipients having the capacity of developing gas after contact with water, the latter on the presence of disintegrating agents having the capacity to swell with water. While many medicaments are incompatible with bicarbonate and/or with acids, the dispersion tablets are the more generally suitable of the two sorts.

Examples of such tablet formulations which are dispersible in water are reported in European Application 181,650B1 published on Aug. 29, 1990 and WO 96/24337 published on Aug. 15, 1996.

Although such water-dispersible tablet formulations have been reported in the literature, such tablets have several deficiencies. They can involve using specially adapted equipment, which is not standard or readily available as in application 181,650, as well as expensive time-consuming procedures for applying an outer protective coating.

Also, it would additionally be highly desirable to provide a tablet formulation that is not only capable of being swallowed or dispersed quickly in water to form a drinkable dispersion, but also is capable of being chewed and rapidly disintegrates in the mouth so that it has a pleasant taste and can be easily swallowed. This is particularly important for those people having trouble swallowing a tablet that is still intact, but yet do not have immediate access to water to disperse the same therein to form a drinkable dispersion.

Cefadroxil monohydrate is a widely used broad spectrum cephalosporin antibiotic that can be administered orally in adults and children. It is sold worldwide by Bristol-Myers Squibb Company under various trade names, including Duricef® and Duracef® in the form of gelatin capsules, uncoated tablets and powder for reconstitution with water to form a liquid suspension, and is dosed several times daily depending on the type of bacterial infection and the patient's needs (i.e. adult, elderly or pediatric).

Therefore, to fulfill the various diverse needs of the patient being treated, and to overcome the aforementioned disadvantages of prior art tablet formulations, it would be highly desirable to provide a tablet of cefadroxil monohydrate that is uncoated (for ease of preparation) and is chewable, swallowable and easily dispersible in water to form a pleasant tasting drinkable dispersion for oral administration to a human being.

It has now surprisingly been found possible to provide such a tablet formulation for cefadroxil monohydrate possessing the aforementioned attributes.

SUMMARY OF THE INVENTION

Accordingly, one embodiment of the invention is an uncoated cefadroxil monohydlrate tablet obtained by direct compression of an anhydrous pharmaceutical composition comprising by weight % based on the final tablet weight:

(a) About 50% of cefadroxil monohydrate;

(b) About 10–12% of a mixture containing 87 parts by weight of microcrystalline cellulose and 13 parts by weight of guar gum;

(c) About 9.5–29% of a cross-linked polyvinylpyrrolidone;

(d) About 2.5–10% of colloidal silicon dioxide;

(e) About 4–19% of dibasic calcium phosphate; and (f) About 9–21% of mannitol or maltitol;

said tablet being capable of oral administration to a human being by swallowing, chewing or disintegrating in water resulting in a drinkable dispersion.

A preferred embodiment is a tablet comprising:

| | |
|---|---|
| (a) Cefadroxil monohydrate | 1000 mg. |
| (b) Cross-linked polyvinylpyrrolidone | 200 mg. |
| (c) Dibasic calcium phosphate | 200 mg. |
| (d) Microcrystalline cellulose/guar gum mixture containing 26 mg. guar gum | 200 mg. |

-continued

| | |
|---|---|
| (e) Mannitol | 350 mg. |
| (f) Colloidal silicon dioxide | 50 mg. |
| (g) Magnesium stearate | 27 mg. |
| (h) Aspartame | 4.5 mg. |
| (i) Sodium saccharine | 4.5 mg. |
| (j) Strawberry aroma | 30 mg. |
| (k) Raspberry aroma | 30 mg. |

DETAILED DESCRIPTION OF THE INVENTION

The compressed tablet is one of the oldest and most popular unit dosage forms for medicinal substances. The tablet as a dosage form can be traced to well over 1,000 years ago when a procedure for molding solid forms containing medicinal ingredients was recorded. As a result of the introduction of new carriers and compression vehicles, tablets are replacing many forms of pills, powders and capsules. Accordingly, tablets presently represent the largest production volume of all pharmaceuticals.

The reasons for the widespread use of tablets are apparent, since tablets facilitate: (1) administration of medication in an accurate dose; (2) fast and accurate dispensing with less chance of error and contamination; (3) ease of administration; (4) administration in a form in which the time and area of contact between the active ingredient and the taste buds are reduced, thus obviating the physiological problems associated with the oral administration of drugs that possess a bitter taste and, in the case of coated tablets, with drugs that possess a disagreeable odor; (5) release of drugs at specific locations in the gastrointestinal tract to prevent degradation of drugs sensitive to the low pH environment in the stomach, prevent release of drugs that irritate the gastric mucosa in the stomach, and facilitate local action or preferential absorption at specific sites in the tract; (6) enhanced stability by effecting a marked reduction in the surface of the drug exposed to the environment; (7) rapid production; and (8) economy and ease in storage, packaging and shipping.

There are currently three basic methods for tableting. They are the wet granulation method, the dry granulation method and the direct compression (DC) method. The direct compression method is by far the desired method from the standpoint of processing time and requirements of equipment and materials. However, only a very limited number of pharmaceutical substances possess enough cohesive strength and flowability to allow direct compression without previous granulation. Certain crystalline materials, such as potassium bromide and potassium chloride can be can be compressed without preliminary treatment. Also, drugs such as aspirin and phenolphthaline can be directly compressed after blending with suitable tableting excipients.

It has been estimated that about 20 percent of the materials used for tableting in the pharmaceutical field may be compressed directly. In order to use this method to a greater extent, many more materials are modified either by treating the material in some special way during early stages of preparation, or by adding a direct compression vehicle, i.e., a dry binder or excipient material which will mix with the active ingredient to provide a flowable powder and form an easily compressible carrier. Exemplary United States patents relating to directly compressible tablets include U.S. Pat. No. 3,584,114 to Cavalli, et al., U.S. Pat. No. 3,725,556 to Hanssen, et al., U.S. Pat. No. 3,873,694 to Kanig, U.S. Pat. No. 4,072,535 to Short, and U.S. Pat. No. 4,439,453 to Vogel.

There are currently several available binders or excipients which can be used as direct compression vehicles. They include spray-dried lactose; anhydrous lactose: microcrystalline cellulose; dibasic calcium phosphate, unmilled; spray-congealed mannitol; ungelatinized starch (e.g., corn starch), and partially or fully pregelatinized starch.

The final tablet of the invention herein will preferably contain about 1 gram of cefadroxil monohydrate active in an approximate 2 gram tablet. Thus, cefadroxil monohydrate accounts for about 50% of the total tablet weight, although this weight % can be greater up to about 70–80%.

The tablet should also contain one or more binding agents or vehicles to promote the direct compression of granular materials into a tablet. Preferably, from about 10–12 weight % of a microcrystalline cellulose/guar gum mixture containing about 13 parts by weight of guar gum with 87 parts of microcrystalline cellulose. Additionally, about 4–19 weight % of dibasic calcium phosphate is used.

The tablet should also contain one or more disintegrating agents or substances that, in the presence of water or biological fluids (e.g. mouth saliva or stomach gastric fluids), promote the release of the active ingredient and the disintegration of the tablet. Preferably, about 9.5–29 weight % of a cross-linked polyvinylpyrrolidone and about 9–21 weight % of mannitol or maltitol is used.

The tablet should also contain one or more glidant materials which are used to improve the flow of the powder blend and to minimize tablet weight variation. Preferably, about 2.5–10 weight % of colloidal silicon dioxide is used.

Additionally, and optionally, other substances commonly used in pharmaceutical formulations can be included such as lubricants (e.g. magnesium stearate) to facilitate ejection of the finished tablet from the dies after compression and to prevent tablets from sticking to the punch faces; flavor enhancers or sweetners (e.g. aspartame, sodium saccharine, strawberry aroma, raspberry aroma, etc.); and dyes or colorants.

Generally, the individual ingredients for the final tablet are first milled, if necessary, to obtain a particle size so that they pass through an 80 mesh U.S. sieve screen (i.e. smaller than 180 $\mu$m). However, the dibasic calcium phosphate and colloidal silicon dioxide need not be specially milled to any particular size.

Also, the cefadroxil monohydrate particle size is preferably such that at least 85% pass through a 120 mesh U.S. sieve screen and at least 50% pass through a 200 mesh U.S. sieve screen.

Although the foregoing invention has been described in some detail for illustration only, it will be readily apparent to one skilled in the art that changes and modifications may be made without departing from the scope of the invention herein.

The following preparation illustrates a particularly preferred embodiment of the invention.

An uncoated direct compression tablet having the following composition was prepared by the procedure described below:

| | |
|---|---|
| (A) Cefadroxil monohydrate | 1000 mg. |
| (B) A mixture containing 174 mg. microcrystalline cellulose and 26 mg. guar gum (Avicel CE ®, FMC Corporation, Newark, Delaware, USA) | 200 mg. |

-continued

|     |                                                                                       |         |
| --- | ------------------------------------------------------------------------------------- | ------- |
| (C) | Anhydrous dibasic calcium phosphate (Encompress ®, Mendell, a Penwest Co., USA)       | 200 mg. |
| (D) | Cross-linked polyvinylpyrrolidone (Crospovidone ® NF, GAF Corporation, USA) (particle size <75 μm) | 200 mg. |
| (F) | Mannitol (particle size <180 μm)                                                      | 350 mg. |
| (F) | Colloidal silicon dioxide (Aerosil ®, Ludeco Co., Belgium) (particle size <180 μm)   | 50 mg.  |
| (G) | Magnesium stearate (particle size <125 μm)                                            | 27 mg.  |
| (H) | Aspartame ® (particle size <180 μm)                                                   | 4.5 mg. |
| (I) | Saccharine (particle size <180 μm)                                                    | 4.5 mg. |
| (J) | Strawberry aroma (particle size <180 μm)                                              | 30 mg.  |
| (K) | Raspberry aroma (particle size <180 μm)                                               | 30 mg.  |
|     | TOTAL WEIGHT                                                                          | 2096 mg.|

Twenty tablets having the composition and particle size characteristics as described above were made by first weighing out the necessary amounts of each ingredient.

Ingredient A (i.e. cefadroxil monohydrate) is first passed through a granulating machine (e.g. Fitzmill U6, made by the Fitzpatrick Co., Elmhurst, Ill., USA) so that 98% of the particles pass through a 120 mesh screen and 70% pass through a 200 mesh screen (U.S. sieve). The Fitzmill machine used a screw feeder operating at 55 RPM and cutters operating at 4600 RPM.

Ingredients A–E were then mixed and blended in a suitable blending machine (e.g. Tubula Type TAZ, made by W. A. Bachofen, Basel, Switzerland) for 10 minutes.

The remaining ingredients F–K are added and the entire mixture is blended an additional 3–4 minutes.

The resulting blend is then compressed into about 20 tablets, each having the weight and composition as set forth above, using a suitable tableting machine (e.g. Erweka Type Eko, Frankfurt, Germany).

The resulting tablets are generally flat, elliptical in shape with scoring lines on the top and bottom, having a length of 23.8 mm, a height of 9.883 mm, a width of 13 mm, and density of 1.2 mg/mm$^3$.

The tablets are swallowable, chewable with a pleasant mouth taste and disintegrate in water in less than 2 minutes to form a pleasant tasting drinkable dispersion.

What is claimed is:

1. An uncoated cefadroxil monohydate tablet obtained by direct compression of an anhydrous pharmaceutical composition comprising by weight % based on the final tablet weight:

(a) About 50% of cefadroxil monohydrate;

(b) About 10–12% of a mixture containing 87 parts by weight of microcrystalline cellulose and 13 parts by weight of guar gum;

(c) About 9.5–29% of a cross-linked polyvinylpyrrolidone;

(d) About 2.5–10% of colloidal silicon dioxide;

(e) About 4–19% of dibasic calcium phosphate; and (f) About 9–21% of mannitol or maltitol;

said tablet being capable of oral administration to a human being by swallowing, chewing or disintegrating in water resulting in a drinkable dispersion.

2. The tablet of claim 1 comprising:

|     |                                                                                      |          |
| --- | ------------------------------------------------------------------------------------ | -------- |
| (a) | Cefadroxil monohydrate                                                               | 1000 mg. |
| (b) | Cross-linked polyvinylpyrrolidone                                                    | 200 mg.  |
| (c) | Dibasic calcium phosphate                                                            | 200 mg.  |
| (d) | Microcrystalline cellulose/guar gum mixture containing 26 mg. guar gum and 174 mg. microcrystalline cellulose. | 200 mg.  |
| (e) | Mannitol                                                                             | 350 mg.  |
| (f) | Colloidal silicon dioxide                                                            | 50 mg.   |
| (g) | Magnesium stearate                                                                   | 27 mg.   |
| (h) | Aspartame                                                                            | 4.5 mg.  |
| (i) | Sodium saccharine                                                                    | 4.5 mg.  |
| (j) | Strawberry aroma                                                                     | 30 mg.   |
| (k) | Raspberry aroma                                                                      | 30 mg.   |

* * * * *